(12) United States Patent
Park et al.

(10) Patent No.: US 11,219,262 B2
(45) Date of Patent: Jan. 11, 2022

(54) SYSTEM AND METHOD FOR PROVIDING SAFETY ASSISTANCE IN VEHICLE

(71) Applicant: Honda Motor Co., Ltd., Tokyo (JP)

(72) Inventors: Leslie Park, Los Angeles, CA (US); Christopher Yee, Redondo Beach, CA (US); Betsy Luk, San Diego, CA (US); Don Herner, Tustin, CA (US); Charles Eddy, Rancho Palos Verdes, CA (US)

(73) Assignee: Honda Motor Co., Ltd., Tokyo (JP)

( * ) Notice: Subject to any disclaimer, the term of this patent is extended or adjusted under 35 U.S.C. 154(b) by 378 days.

(21) Appl. No.: 16/541,555

(22) Filed: Aug. 15, 2019

(65) Prior Publication Data
US 2021/0045486 A1 Feb. 18, 2021

(51) Int. Cl.
| | | |
|---|---|---|
| G08B 1/00 | (2006.01) | |
| A42B 3/04 | (2006.01) | |
| H04W 4/021 | (2018.01) | |
| G06F 1/16 | (2006.01) | |
| A61B 5/00 | (2006.01) | |
| G06F 3/01 | (2006.01) | |
| G08B 25/01 | (2006.01) | |
| A41D 13/018 | (2006.01) | |
| H05B 47/105 | (2020.01) | |
| H04W 4/02 | (2018.01) | |

(52) U.S. Cl.
CPC .......... *A42B 3/0486* (2013.01); *A41D 13/018* (2013.01); *A42B 3/046* (2013.01); *A61B 5/6803* (2013.01); *G06F 1/163* (2013.01); *G06F 3/015* (2013.01); *G08B 25/016* (2013.01); *H04W 4/021* (2013.01); *A61B 5/0006* (2013.01); *H04W 4/027* (2013.01); *H05B 47/105* (2020.01)

(58) Field of Classification Search
CPC ..... A42B 3/0486; A42B 3/046; A42B 5/6803; A42B 5/0006; A42B 3/30; A41D 13/018; G06F 1/163; G06F 3/015; G08B 25/016; H05B 47/105; H04W 4/38; H04W 4/021; H04W 4/027
USPC ............ 340/532, 540, 432, 436, 576, 573.1
See application file for complete search history.

(56) References Cited

U.S. PATENT DOCUMENTS

| | | | |
|---|---|---|---|
| 6,951,033 B2 | 10/2005 | Dainese | |
| 8,505,670 B2 | 8/2013 | Ogawa et al. | |
| 9,750,429 B1 | 9/2017 | Sackner et al. | |
| 2007/0038057 A1 | 2/2007 | Nam et al. | |
| 2013/0325089 A1* | 12/2013 | Divani ................. | A61F 7/0085 607/104 |
| 2015/0057984 A1 | 2/2015 | Nicoletti et al. | |
| 2016/0120238 A1* | 5/2016 | Duncan ............... | A41D 13/018 2/462 |
| 2016/0331316 A1* | 11/2016 | Allen .................... | G01P 15/02 |

(Continued)

*Primary Examiner* — Anh V La
(74) *Attorney, Agent, or Firm* — American Honda Motor Co., Inc.; Aaron Fong (57) ABSTRACT

A system for providing safety assistance in a vehicle. The system includes a helmet and a first plurality of sensors in the helmet. The system further includes control circuitry that captures a first plurality of signals from the first plurality of sensors in the helmet. The first plurality of signals indicates first motion information corresponding to the helmet. The control circuitry further controls one of an inflation element or a hardening element disposed in a wearable garment based on a determination that the first motion information corresponding to the helmet exceeds a first predefined threshold.

15 Claims, 6 Drawing Sheets

(56) References Cited

U.S. PATENT DOCUMENTS

| | | | |
|---|---|---|---|
| 2018/0064199 A1* | 3/2018 | Battis | A42B 3/286 |
| 2018/0116543 A1* | 5/2018 | Miller | G16H 20/00 |
| 2018/0368490 A1* | 12/2018 | Suddaby | A63B 71/1291 |
| 2019/0166945 A1* | 6/2019 | Martin | A42B 3/28 |
| 2019/0268550 A1* | 8/2019 | Arnold | A42B 3/0433 |

* cited by examiner

SYSTEM AND METHOD FOR PROVIDING SAFETY ASSISTANCE IN VEHICLE

BACKGROUND

Various safety techniques are being developed for riders of different vehicles. One of the examples for such safety techniques is a utilization of a helmet. Typically, the helmet may protect certain body parts (for example head, neck) of the riders during the collisions or accidents while driving the vehicle. However, in certain situations, such as high-speed collisions, wearing of the helmet may not provide safety to other body parts of the rider. Thus, there is a need for a smart system which may provide real-time safety assistance to the riders during driving and enhance overall driving experience of the rider.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

An exemplary aspect of the disclosure provides a system to provide safety assistance in a vehicle. The system may include a helmet. The system may further include a first plurality of sensors in the helmet. The system may further include control circuitry configured to capture a first plurality of signals from the first plurality of sensors in the helmet. The first plurality of signals may indicate first motion information corresponding to the helmet. The control circuitry may further control one of an inflation element or a hardening element disposed in a wearable garment based on a determination that the first motion information corresponding to the helmet exceeds a first predefined threshold.

Another exemplary aspect of the disclosure provides an electronic control device to provide safety assistance in a vehicle. The electronic control device may include control circuitry communicably coupled with a headgear and a wearable garment. The control circuitry may be configured to capture a first plurality of signals from a first plurality of sensors in the headgear. The first plurality of signals may indicate first motion information corresponding to the headgear. The control circuitry may further control one of an inflation element or a hardening element disposed in the wearable garment based on a determination that the first motion information corresponding to the headgear exceeds a first predefined threshold.

Another exemplary aspect of the disclosure provides a method for providing safety assistance in a vehicle. Any computing device, for example, control circuitry, may execute operations specified in the method. The method may include capturing a first plurality of signals from a first plurality of sensors in a helmet. The first plurality of signals may indicate first motion information corresponding to the helmet. The method may further include controlling one of an inflation element or a hardening element disposed in a wearable garment based on a determination that the first motion information corresponding to the helmet exceeds a first predefined threshold.

This summary is provided to introduce a selection of concepts in a simplified form that are further disclosed in the detailed description of the present disclosure. This summary is not intended to identify key or essential inventive concepts of the claimed subject matter, nor is it intended for determining the scope of the claimed subject matter.

The foregoing summary, as well as the following detailed description of the present disclosure, is better understood when read in conjunction with the appended drawings. For the purpose of illustrating the present disclosure, exemplary constructions of the preferred embodiment are shown in the drawings. However, the present disclosure is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION

The following described implementations may be found in a disclosed system to provide safety assistance in a vehicle. Exemplary aspects of the disclosure provide the system which may include a helmet. The helmet may control a wearable garment worn by a rider of the vehicle and provide real-time safety assistance to the rider during different situations, for example, collisions or accidents. The helmet may include a first plurality of sensors that may be configured to capture a first plurality of signals. The system may further include control circuitry that may capture the first plurality of signals from the first plurality of sensors in the helmet. The first plurality of signals may indicate first motion information (for example acceleration information) corresponding to the helmet or the rider. In case, the first motion information exceeds a first predefined threshold (for example threshold to detect the collision or accident impact), the control circuitry may further control one of an inflation element or a hardening element disposed in the wearable garment worn by the rider. The inflation element may inflate the wearable garment to further dampen the collision impact on the rider. Further, the hardening element in the wearable garment may include an electric fiber (for example) that may harden the wearable garment based on the detection of the collision.

In another embodiment, the wearable garment may include a plurality of tubes which may include a treatment fluid. The plurality of tubes may be disposed near different body parts (for example knee, elbow, neck, spin, etc) of the rider. Based on the detection of the collision or accident by the first motion information, the disclosed system may further control the temperature (i.e. heat or cool) of the treatment fluid to provide real-time safety and medical assistance to different body parts of the rider. The disclosed system further includes an image capturing device and a location sensor to capture images of the surroundings and current geo-location of the vehicle. In case of detection of impact of the collision or accident based on the first motion information, the control circuitry may transmit the captured images or the geo-location to other nearby vehicles (or to medical agencies like hospitals) to get further assistance. Thus, the disclosed system detects the collisions or accidents based on the plurality of sensors in the helmet, controls different elements (for example inflation element, hardening element, treatment fluid, etc) in the wearable garment and further transmits the real-time data (for example captured images, geo-location of the rider) to provide real-time and enhanced safety assistance to the rider of the vehicle.

Reference will now be made in detail to specific aspects or features, examples of which are illustrated in the accompanying drawings. Wherever possible, corresponding or similar reference numbers will be used throughout the drawings to refer to the same or corresponding parts.

Figure 1:
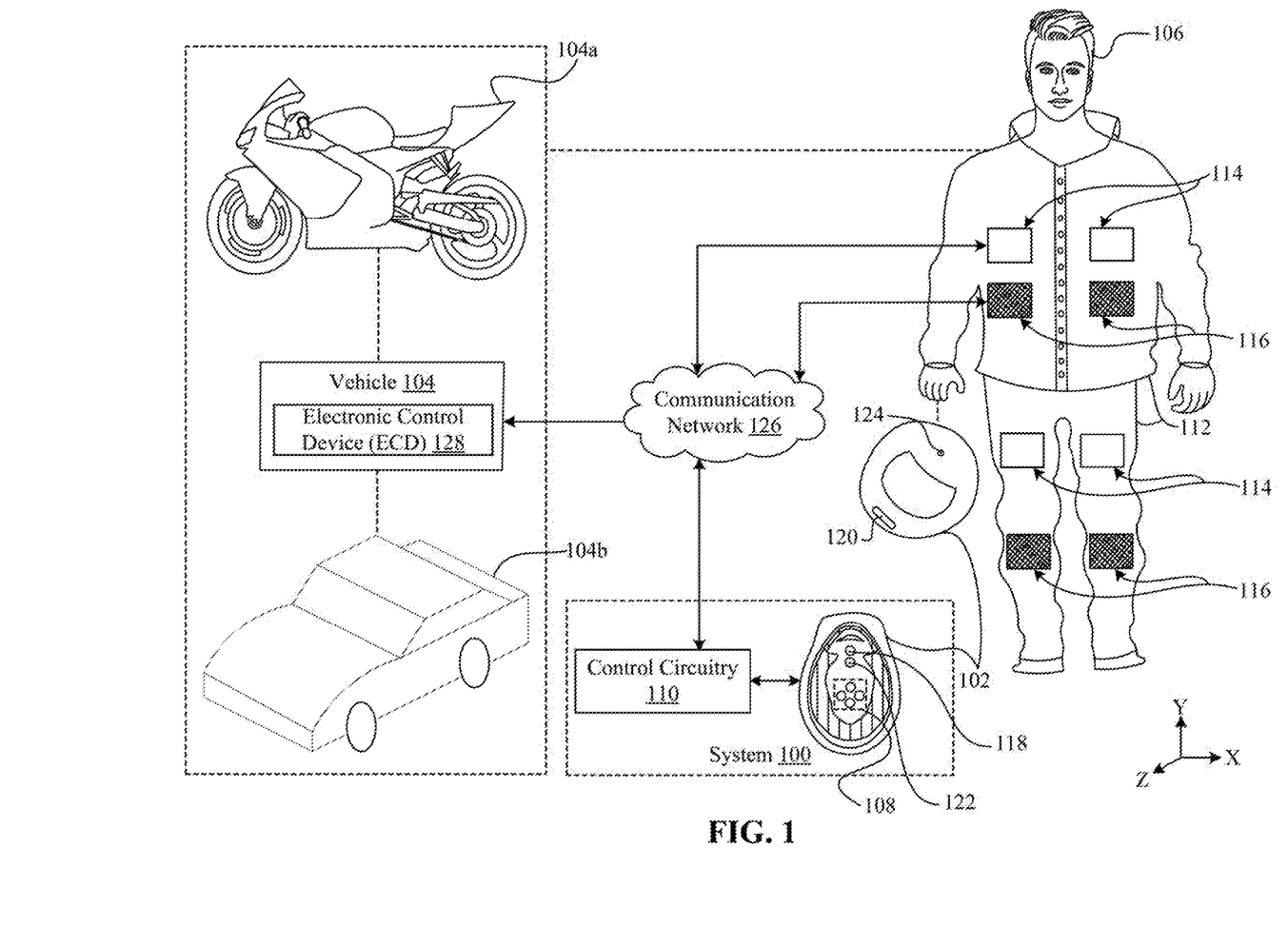
FIG. 1 illustrates an exemplary environment for providing safety assistance in a vehicle, in accordance with an embodiment of the disclosure.

FIG. 1 illustrates an exemplary environment for providing safety assistance in a vehicle, in accordance with an embodiment of the disclosure. With reference to FIG. 1, there is shown an exemplary environment. The exemplary environment may include a system 100 which may further include a helmet 102. The exemplary environment may further include a vehicle 104. The helmet 102 may provide safety assistance to a rider 106 associated with the vehicle 104. In some embodiments, the helmet 102 may also provide safety assistance to a passenger (not shown) in the vehicle 104. As shown in FIG. 1, the system may further include control circuitry 110 communicably coupled with the helmet 102 and a wearable garment 112 (for example worn by the rider 106). In some embodiment, the control circuitry 110 may be included in the helmet 102.

The helmet 102 may include a first plurality of sensors 108, a temperature sensor 118, an image capturing device 120, a location sensor 122, and a lighting element 124. The wearable garment 112 may include an inflation element 114 and a hardening element 116. The exemplary environment of FIG. 1 may further include a communication network 126. The control circuitry 110, the vehicle 104 and the wearable garment 112 may communicated with each other through the communication network 126. It may be noted that the rider 106 shown in FIG. 1 is merely an example. The present disclosure may be also applicable to other types of rider 106 such as people of different genders and age, without limiting the scope of the disclosure.

The helmet 102 may primarily act as a protective gear for the rider 106 of the vehicle 104 in the course of the journey. Also, the helmet 102 may act as a housing for different components of the system 100. In accordance with an embodiment, the helmet 102 may also act as a housing for the first plurality of sensors 106 and a support structure for other components of the system 100. The helmet 102 depicted in FIG. 1 is an example of a full-face helmet. However, the present disclosure may be also applicable to other types of a motorcycle helmet, such as a modular helmet (or a flip-up helmet), an open-face helmet (also referred to as a "¾" helmet), a half helmet, an off-road helmet, and a sports helmet or different types of headgears.

The vehicle 104 may be a non-autonomous vehicle, a semi-autonomous vehicle, or a fully autonomous vehicle, for example, as defined by National Highway Traffic Safety Administration (NHTSA). Examples of the vehicle 104 may include, but are not limited to, a two-wheeler vehicle 104A, a three-wheeler vehicle, a four-wheeler vehicle 104B, a hybrid vehicle, or a vehicle with autonomous drive capability that uses one or more distinct renewable or non-renewable power sources. A vehicle that uses renewable or non-renewable power sources may include a fossil fuel-based vehicle, an electric propulsion-based vehicle, a hydrogen fuel-based vehicle, a solar-powered vehicle, and/or a vehicle powered by other forms of alternative energy sources. The vehicle 104 may be a system through which the rider 106 may travel from a start point to a destination point Examples of the two-wheeler vehicle 104A may include, but are not limited to, an electric two-wheeler, an internal combustion engine (ICE)-based two-wheeler, or a hybrid two-wheeler. Similarly, examples of the four-wheeler vehicle 104B may include, but are not limited to, an electric car, an internal combustion engine (ICE)-based car, a fuel-cell based car, a solar powered-car, or a hybrid car. It may be noted here that the two-wheeler vehicle 104A and the four-wheeler vehicle 104B are merely shown as examples in FIG. 1. The present disclosure may be also applicable to other types of two-wheelers (e.g., a scooter) or four-wheelers. The description of other types of the vehicle 104 has been omitted from the disclosure for the sake of brevity.

The first plurality of sensors 108 may include suitable logic, circuitry, and/or interfaces that may configured to capture a first plurality of signals. The first plurality of signals may indicate first motion information corresponding to the helmet 102. The first motion information may indicate a sudden change in acceleration, speed or force (in one of a X-direction, a Y-direction, or a Z-direction) of the helmet 102 or the vehicle 104. The first motion information may be used by the system 100 to detect an impact or shock related to an accident or collision with the helmet 102. Examples of the first motion information may include, but are not limited to, acceleration information, speed information, a G-force information, or elevation information. Examples of the first plurality of sensors 108 may include, but are not limited to, an acceleration sensor, a speed sensor, a G-force sensor, a vibration sensor, an impact sensor, a shock sensor, or an elevation sensor. It may be noted that the position, arrangement and numbers of the first plurality of sensors 108 shown in FIG. 1 is merely an example. The present disclosure may be also applicable to other positions, arrangements, and numbers the first plurality of sensors 108, without a deviation from scope of the disclosure.

In some embodiments, one or more of the first plurality of sensors 108 may act as an electrode to capture a plurality of brainwave signals (as the first plurality of signals) from a head of the rider 106. In such case, the first plurality of sensors 108 may be present non-invasively at different locations in the helmet 102. Alternatively stated, the first plurality of sensors 108 may be in the helmet 102 with a contactless arrangement over the head of the rider 106. Alternatively, the first plurality of sensors 108 may be invasive electrodes or electrodes that contact the head of the rider 106 at different locations. The location of the first plurality of sensors 108 may be in relation to different cortical areas of the brain of the rider 106.

The control circuitry 110 may include suitable logic, circuitry, and interfaces that may be configured to execute program instructions associated with different operations to be executed by the system 100. For example, some of the operations may include capture of the first plurality of signals from the first plurality of sensors 108 and control one of the inflation element 114 and/or the hardening element 116 disposed in the wearable garment 112 based on the captured first plurality of signals. The control circuitry 110 may include one or more specialized processing units, which may be implemented as a separate processor. In an embodiment, the one or more specialized processing units may be implemented as an integrated processor or a cluster of processors that perform the functions of the one or more specialized processing units, collectively. The control circuitry 110 may be implemented based on a number of processor technologies known in the art. Examples of the control circuitry 110 may include, but are not limited to, an x86-based processor, a Graphical Processing Unit (GPU), a Reduced Instruction Set Computer (RISC) processor, an Application Specific Integrated Circuit (ASIC) processor, a Complex Instruction Set Computer (CISC) processor, a microcontroller, a Central Processing Unit (CPU), and/or a combination thereof. Although in FIG. 1, the control circuitry 110 is separated from the helmet 102. However, in some embodiments, the control circuitry 110 may be integrated in the helmet 102, without a deviation from the scope of the disclosure.

The wearable garment 112 may be a textile product which may be worn by the rider 106. The wearable garment 112 may be worn on a complete body of the rider 106 or may cover certain body parts of the rider 106. The wearable garment 112 may be made of different combination of materials, for example textile, animal skin, or the like. Examples of the wearable garment 112 may include, but are not limited to, a jacket, a blazer, a shirt, a trouser, an inner wear, a pant, or a combination. It may be noted that the wearable garment 112 shown in FIG. 1 is merely an example. The present disclosure may be also applicable to other types of wearable garments, without a deviation from scope of the disclosure. In some embodiments, the wearable garment 112 may include a communication interface (not shown) or a processor (not shown) to communicate with the system 100 or the control circuitry 110 through the communication network 126 (i.e. wired connection or a wireless connection).

The temperature sensor 118 may be configured to detect a change in temperature in the helmet 102. The temperature sensor 118 may be further configured to convert the detected temperature or the change in temperature into an electrical signal which may be further provided to the control circuitry 110. The control circuitry 110 may be configured to detect sudden change in temperature (for example during the accident) inside the helmet 102 based on the electrical signal received from the temperature sensor 118. Examples of the temperature sensor 118 may include, but are not limited to, a thermistor, a resistance temperature detector (RTD), a thermocouple, semiconductor-based temperature sensor, a thermostat, a thermometer, or the like.

The image capturing device 120 may include suitable logic, circuitry, and/or interfaces that may be configured to capture one or more images of surroundings of the helmet 102 of the rider 106 and/or the passenger. The image capturing device 120 may be positioned on an outer surface (for example front side as shown in FIG. 1) of the helmet 102 to capture the one or more images of the surroundings. In some embodiments, the image capturing device 120 may be disposed on the wearable garment 112 or on the vehicle 104. Examples of the image capturing device 120 may include, but are not limited to, an image sensor, a wide-angle camera, an action camera, a closed-circuit television (CCTV) camera, a camcorder, a digital camera, camera phones, a time-of-flight camera (ToF camera), a night-vision camera, and/or other image capture devices. In some embodiments, the helmet 102 may include a plurality of image capturing devices (not shown) arranged at different positions of the outer surface of the helmet 102. In some embodiments, the image capturing device 120 may be a 360-degree camera which may be configured to capture a 360-degree view of the surroundings of the helmet 102. In accordance with an embodiment, the 360-degree camera may further include a plurality of image sensors (not shown) to capture the 360-degree view of the surroundings of the helmet 102.

The location sensor 122 may include suitable logic, circuitry, and/or interfaces that may be configured to determine a current geo-location of the helmet 102 or the vehicle 104. Examples of the location sensor 122, may include, but are not limited to, a Global Navigation Satellite System (GNSS)-based sensor of the vehicle 104. Examples of the GNSS-based sensor may include, but are not limited to, global positioning sensor (GPS), Global Navigation Satellite System (GLONASS), or other regional navigation systems or sensors.

The lighting element 124 may include suitable logic, circuitry, and/or interfaces that may be configured to emit a light or a lightening pattern (for example blinking or flashing in a defined pattern). The lighting element 124 may be controlled by the control circuitry 110 based on the determination of the accident or the collision based on the first motion information. The lighting element 124 may be disposed on the outer surface of the helmet 102. In some embodiments, the lighting element 124 may be disposed on the wearable garment 112 or on the vehicle 104. Example of the lighting element 124 may include, but are not limited to, a light bulb, a light emitting diode (LED), and the like.

It may be noted here that the positions, arrangements, or shapes of the temperature sensor 118, the image capturing device 120, the location sensor 122, and the lighting element 124 shown in FIG. 1 is merely an example. The present disclosure may be also applicable to other positions, arrangements, shapes, or structure of temperature sensor 118, the image capturing device 120, the location sensor 122, and the lighting element 124, without a deviation from scope of the disclosure.

The communication network 126 may be a communication medium through which the system 100, the vehicle 104, and the wearable garment 112 in the network environment may communicate with each other. The communication network 126 may be one of a wired connection or a wireless connection. Examples of the communication network 126 may include, but are not limited to, internet, Internet-based mobile ad hoc networks (IMANET), a cellular network, such as a 3G, 4G, or 5G network, a cloud network, and/or a Wide Area Network (WAN). Various devices or components in the system 100, the vehicle 104, and the wearable garment 112 may connect to the communication network 126 in accordance with various wireless communication protocols. Examples of such wireless communication protocols may include, but are not limited to, IEEE 802.11, 802.11x, 802.15, 802.16, 1609, Worldwide Interoperability for Microwave Access (Wi-MAX), Wireless Access in Vehicular Environments (WAVE), cellular communication protocols, Transmission Control Protocol and Internet Protocol (TCP/IP), User Datagram Protocol (UDP), Hypertext Transfer Protocol (HTTP), LTE, File Transfer Protocol (FTP), ZigBee, EDGE, Li-Fi, and/or other wireless communication protocols.

In operation, the control circuitry 110 may be configured to control the first plurality of sensors 108 to capture the first plurality of signals which may indicate the first motion information corresponding to the helmet 102. The control circuitry 110 may be further configured to determine the impact of accident, shock, or collision with the helmet 102 based on the determination that the first motion information exceeds a first predefined threshold. The first predefined threshold may be a pre-defined motion information to indicate the impact of accident or collision with the helmet 102. The details of the first motion information and the first predefined threshold may be described in detail, for example, in FIG. 3A. The control circuitry 110 may be further configured to control the inflation element 114 or the hardening element 116 disposed in the wearable garment 112 based on the determination of the accident or collision. In other words, the control circuitry 110 may be further configured to control the inflation element 114 or the hardening element 116 based on the determination that the first motion information of the passenger exceeds the first predefined threshold. The inflation element 114 may inflate the wearable garment 112 or the hardening element 116 may harden or make rigid different portions of the wearable garment 112 to protect the rider 106 from the impact of the detected accident on the real-time basis. The details of the inflation or hardening of the wearable garment 112 is described in detail, for example, in FIGS. 3A, 3B, 4A, and 4B. In FIG. 1, there is further shown an electronic control device 128 in the vehicle 104. The electronic control device 128 may be configured to control the vehicle 104. The details of the electronic control device 128 is described in detail, for example, in FIG. 5.

Figure 2:
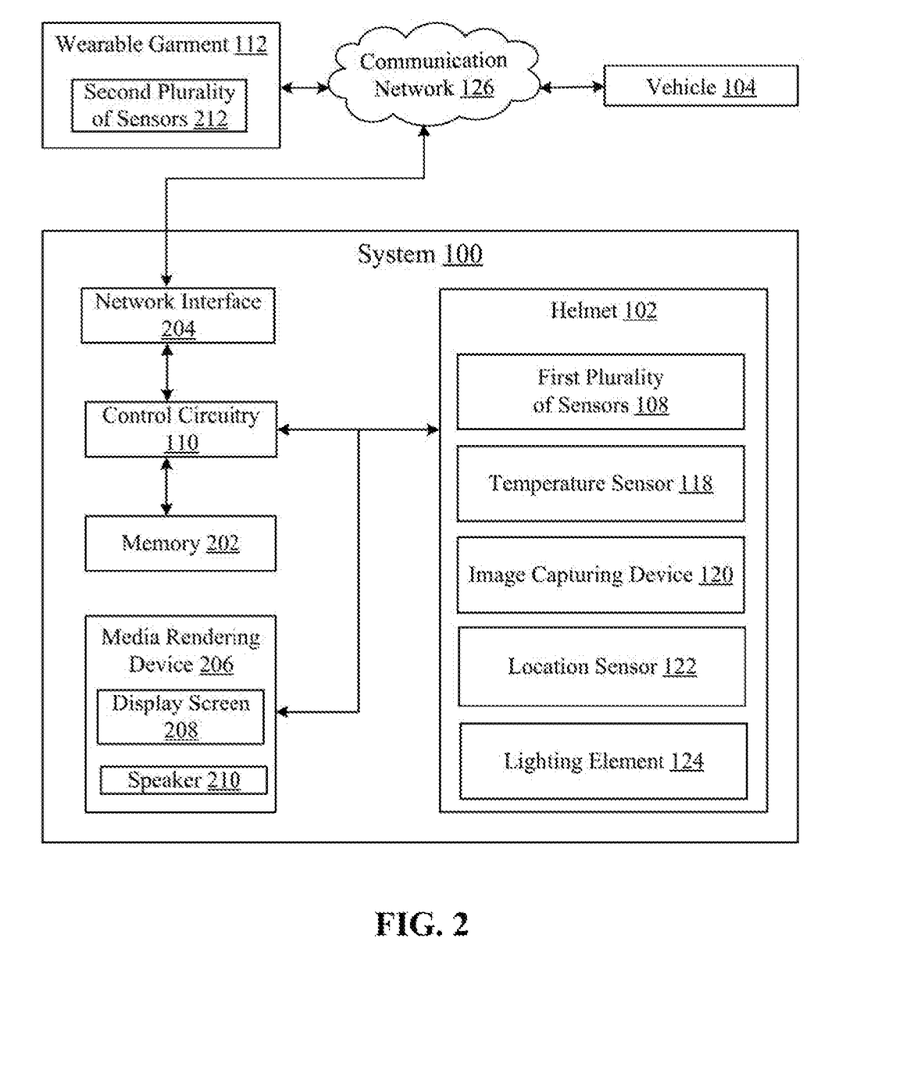
FIG. 2 illustrates a block diagram of an exemplary system for providing safety assistance in a vehicle, in accordance with an embodiment of the disclosure.

FIG. 2 illustrates a block diagram of an exemplary system for providing safety assistance in a vehicle, in accordance with an embodiment of the disclosure. FIG. 2 is explained in conjunction with elements from FIG. 1. With reference to FIG. 2, there is shown the system 100. The system 100 may include the control circuitry 110, the helmet 102, a memory 202, a network interface 204, and a media rendering device 206. The helmet may further include the first plurality of sensors 108, the temperature sensor 118, the image capturing device 120, the location sensor 122, and the lighting element 124. As further shown in FIG. 2, the media rendering device 206 may include a display screen 208 and a speaker 210. The control circuitry 110 may be connected to the memory 202, the network interface 204, the media rendering device 206 and the helmet 102 through wired or wireless connections.

The memory 202 may include suitable logic, circuitry, and/or interfaces that may store a set of instructions executable by the control circuitry 110. The memory 202 may be configured to store the captured first plurality of signals captured from the first plurality of sensors 108 in the helmet 102, a second plurality of signal captured from a second plurality of sensors 212 disposed on the wearable garment 112. In some embodiments, the memory 202 may be configured to store the first predefined threshold to be compared with the first motion information. The memory 202 may further store a predefined media content to be rendered on the media rendering device 206. In some embodiments, the memory 202 may be configured to store the one or more images captured by the image capturing device 120 and the current geo-location determined by the location sensor 122. The memory 202 may be a persistent storage medium, a non-persistent storage medium, or a combination thereof. Examples of implementation of the memory 202 may include, but are not limited to, Random Access Memory (RAM), Read Only Memory (ROM), Hard Disk Drive (HDD), Solid State Drive (SSD), flash memory, cache memory, and/or a Secure Digital (SD) card.

The network interface 204 may include suitable logic, circuitry, and/or interfaces that may enable communication among the system 100 and other external devices, such as the wearable garment 112, or an electronic control device 128 of the vehicle 104, via the communication network 126. The network interface 204 may implement known technologies to support wired and/or wireless communication via the communication network 126. The network interface 204 may include, but is not limited to, an antenna, a frequency modulation (FM) transceiver, a radio frequency (RF) transceiver, one or more amplifiers, a tuner, one or more oscillators, a digital signal processor, a coder-decoder (CODEC) chipset, a subscriber identity module (SIM) card, and/or a local buffer.

The network interface 204 may communicate via wired and/or wireless communication with networks, such as the Internet, an Intranet and/or a wireless network, such as a cellular telephone network, a wireless local area network (LAN) and/or a metropolitan area network (MAN). The communication may use any of a plurality of communication standards, protocols and technologies, such as Long Term Evolution (LTE), Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

The media rendering device 206 may include suitable logic, circuitry, and/or interfaces that may be configured to render the predefined media content on one of the display screen 208 or the speaker 210. The display screen 208 may be configured to display the predefined media content (for example a photograph or a movie) based on a command received from the control circuitry 110. The display screen 208 may be realized through several known technologies such as, but not limited to, at least one of a Liquid Crystal Display (LCD) display, a Light Emitting Diode (LED) display, a plasma display, or an Organic LED (OLED) display technology, or other display devices. In accordance with an embodiment, the display screen 208 may refer to a display screen of a head mounted device (HMD), a smart-glass device, a see-through display, a projection-based display, an electro-chromic display, or a transparent display. The speaker 210 may be configured to output the predefined media content (for example a musical tone or a song) as audio output based on a command received from the control circuitry 110. Examples of the speaker 210 may include, but are not limited to, a loudspeaker, a woofer, a sub-woofer, a tweeter, a wireless speaker, a monitor speaker, or other speakers or sound output device.

In FIG. 2, there is further shown a second plurality of sensors 212 included in or disposed on the wearable garment 112. The functions of the second plurality of sensors 212 may be same as the functions of the first plurality of sensors 108 disposed on or inside the helmet 102. Each of the second plurality of sensors 212 of the wearable garment 112 may be associated with a particular body part (for example knee, elbow, neck, feet, spin, etc) of the rider 106. In some embodiments, each of the second plurality of sensors 212 may be disposed in proximity to the corresponding body part of the rider 106. The second plurality of sensors 212 may be configured to capture a second plurality of signals where each of the second plurality of signals may indicate second motion information corresponding to each of the second plurality of sensors 212. The second motion information may indicate the sudden change in acceleration, speed or force (in one of a X-direction, a Y-direction, or a Z-direction) detected by the second plurality of sensors 212 near different body parts of the rider 106. Similar, to the first motion information, the second motion information may be used by the system 100 to detect an impact or shock related to an accident or collision with the wearable garment 112 in case the second motion information exceeds a second predefined threshold (similar to the first predefined threshold). Thus, even though the helmet 102 is not worn by the rider 106, the system 100 may be able to detect the accident based on the second plurality of sensors 212 on the wearable garment 112 and control one of the inflation element 114 or the hardening element 116 to protect the rider 106 from the impact of the accidents on the real-time basis.

Figure 3A:
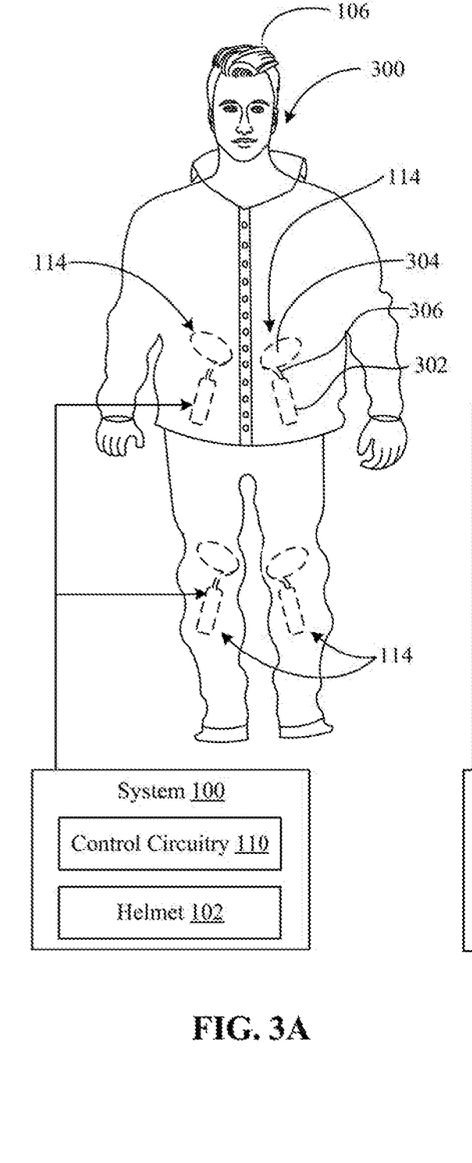
FIGS. 3A and 3B collectively illustrate an exemplary scenario for inflation of a wearable garment controlled by the system of FIG. 2, in accordance with an embodiment of the disclosure.
Figure 3B:
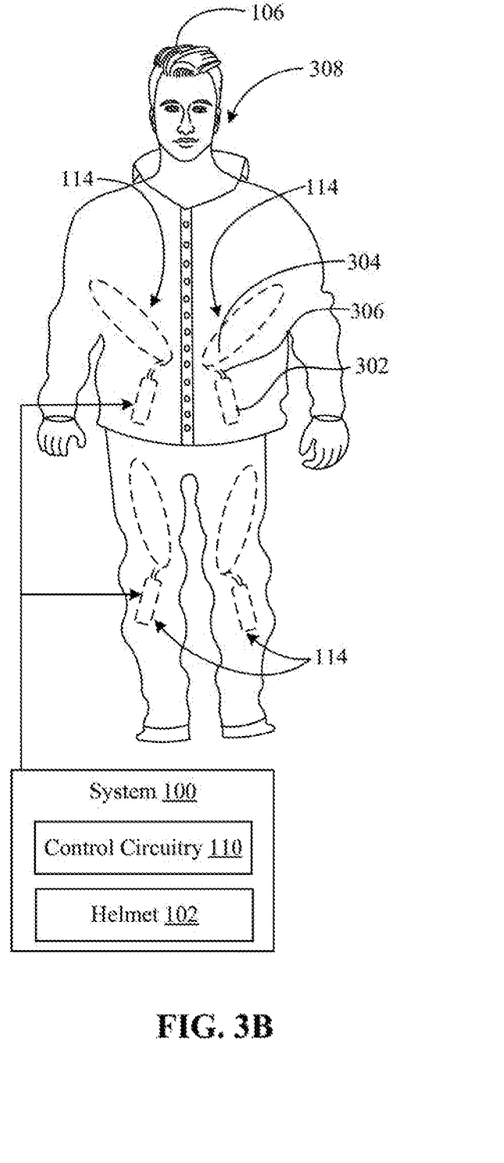

FIGS. 3A and 3B collectively illustrate an exemplary scenario for inflation of a wearable garment controlled by the system of FIG. 2, in accordance with an embodiment of the disclosure. FIG. 3A is explained in conjunction with elements from FIGS. 1 and 2. With reference to FIG. 3A, there is shown a first scenario 300 in which the wearable garment 112, worn by the rider 106, may be in a non-inflated state.

As shown in FIG. 3A, the wearable garment 112 may include the inflation element 114. The inflation element 114 may include a gas cylinder 302, an inflation chamber 304, and a pressure tubing 306 that may couple the gas cylinder 302 and the inflation chamber 304. In the non-inflated state, the gas cylinder 302 and the corresponding inflation chamber 304 may be in a normal state. In the normal state, the inflation chamber 304 may not be supplied with pressurized gas by the gas cylinder 302 and may not be inflated. The positions of the inflation element 114 shown in FIG. 3A, is merely an example. The wearable garment 112 may include multiple inflation elements disposed at different positions or places of the wearable garment 112, without any deviation from scope of the disclosure.

In accordance with an embodiment, the control circuitry 110 may be configured to determine the accident or collision with the helmet 102 based on the captured first motion information as described in FIG. 1. The control circuitry 110 may be configured to compare the captured first motion information with the first predefined threshold to determine the impact of the accident with the helmet 102. For example, the first predefined threshold may be a value in Hertz (in case the first motion information may be considered as vibration), in meter per second (in case the first motion information may be considered as acceleration or speed) or in Newton (in case the first motion information may be considered as G-force). In some embodiments, the control circuitry 110 may be configured to detect sudden change in acceleration, (or G-force, or vibration) with the helmet 102 based on the comparison of the captured first motion information (i.e. indicated by the first plurality of signals) with the first predefined threshold and further determine the accident of collision.

In accordance with an embodiment, the control circuitry 110 may be further configured to control the inflation element 114 based on the detected accident or the collision with the helmet 102 to convert the inflation element 114 from the non-inflated state to an inflated state. In the inflated state, the control circuitry 110 may be further configured to control the gas cylinder 302 of the inflation element 114 to inflate the inflation chamber 304 (as shown in a second scenario 308 in FIG. 3B) based on the determination of the accident or collision with the helmet 102. In the inflated state, the control circuitry 110 may trigger the gas cylinder 302 to release pressurized gas (not shown) to the inflation chamber 304 through the pressure tubing 306. The inflation of the pressurized gas in the inflation chamber 304 (shown in FIG. 3B) may air-cushion the complete or particular portion the wearable garment 112 worn by the rider 106. Examples of the inflation chamber 304 may include, but not limited to, an elastic bag or a rubber bag that expands on admission of pressurized gas.

The control circuitry 110 may control the gas cylinder 302 through a suitable control element (not shown) that may trigger the pressurized gas to the inflation chamber 304 during the determination of the collision with the helmet 102. Examples of the suitable control element may include, but are not limited to, a solenoid, or a digital valve controller, and the like. In other embodiment, the pressurized gas in the gas cylinder 302 may also be used to suppress fire during the collision. Examples of the pressurized gas may include, but are not limited to, argon, carbon dioxide, and the like. In some embodiments, the control circuitry 110 may be configured to provide a signal (for example a control signal) to control the gas cylinder 302 to trigger the pressurized gas to the inflation chamber 304.

The portions of the wearable garment 112 inflated may be based on the positions of the inflation element 114 in the wearable garment 112. In case of multiple inflation elements disposed in the wearable garment 112, different portions of the wearable garment 112 may be inflated. Thus, different body parts (i.e. chest, spin, shoulder, neck, stomach, knees, etc) of the rider 106 close to different inflation elements may be protected or secured from the impact of the collision or accident. The inflation element 114 shown in FIG. 3A is merely an example. The present disclosure may be also applicable to other types of the inflation element 114, without a deviation from scope of the disclosure.

Figure 4A:
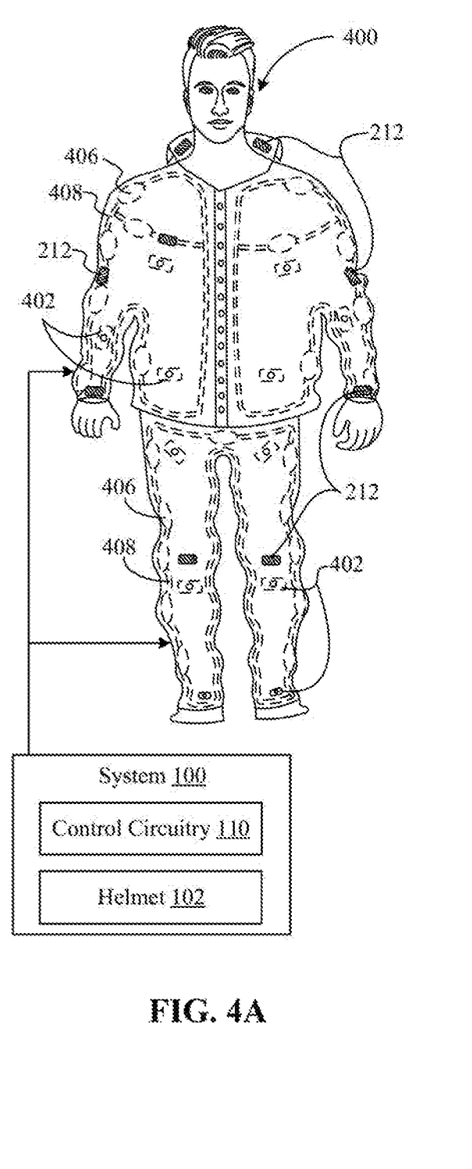
FIGS. 4A and 4B collectively illustrate an exemplary scenario for hardening of a wearable garment controlled by the system of FIG. 2, in accordance with an embodiment of the disclosure.
Figure 4B:
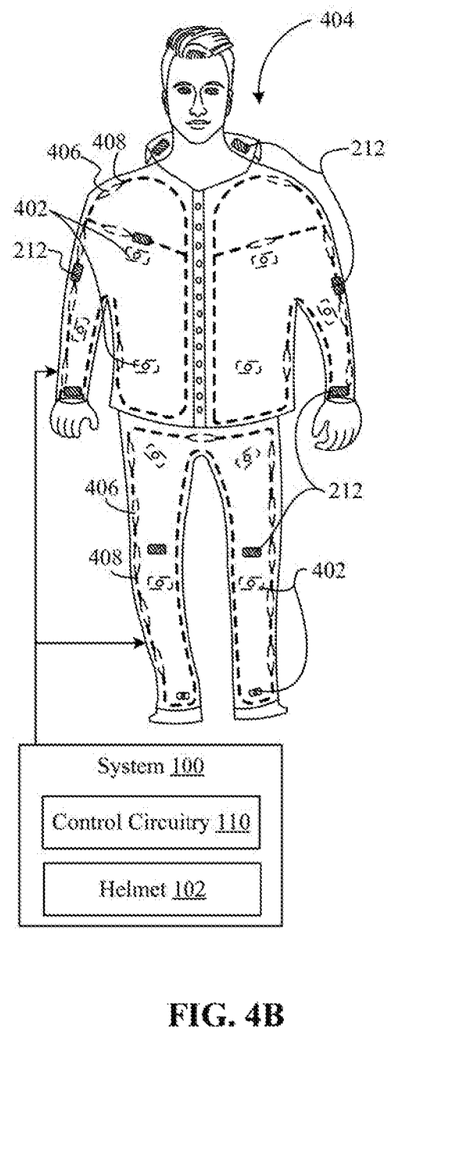

FIGS. 4A and 4B collectively illustrate an exemplary scenario for hardening of a wearable garment controlled by the system of FIG. 2, in accordance with an embodiment of the disclosure. FIG. 4A is explained in conjunction with elements from FIGS. 1, 2, 3A, and 3B. With reference to FIG. 4A, there is shown a third scenario 400 in which the wearable garment 112, worn by the rider 106, may be in a non-hardening state (or a loose or flexible state). In the non-hardening state, the wearable garment 112 may in a normal state which may be a state during the regular movement (i.e. without any detection of accident) of the vehicle 104. During the detection of the accident or collision (either based on the first motion information detected by the first plurality of sensors 108 or the second plurality of sensors 212), the control circuitry 110 may be configured to control the hardening element 116 to convert the wearable garment 112 from the non-hardening state to a hardening state (as shown in a fourth scenario 404 in FIG. 4B).

As shown in FIG. 4A, the hardening element 116 may include an electric fiber 402 woven on the wearable garment 112. In accordance with an embodiment, the control circuitry 110 may be configured to determine the accident or collision with the helmet 102 based on the captured first motion information as described in FIG. 1. The control circuitry 110 may be further configured to control the hardening element 116 based on the detected accident or the collision with the helmet 102 to convert the hardening element 116 from the non-hardening state to the hardening state. In the hardening state, the control circuitry 110 may be configured to supply electric power to the electric fiber 402 of the hardening element 116 and may control rigidness of the electric fiber 402 to control the rigidness of the wearable garment 112 as shown in the fourth scenario 404 in FIG. 4B. The electric fiber 402 of the hardening element 116 may harden the wearable garment 112 to protect different body parts of the rider 106 from the impact of the accident or collision. Examples of the electric fiber 402 may include, but are not limited to, a heat responsive electric fiber, or a bimetal, and the like. It may be noted that the electric fiber 402 shown in FIGS. 4A and 4B at different positions (for example knee, elbow, chest, etc) is merely an example. The present disclosure may be also applicable to other types of electric fiber 402 positioned at different places of the wearable garment 112, without a deviation from scope of the disclosure.

In accordance with an embodiment, the hardening element 116 of the wearable garment 112 may include a plurality of fluid capsules 406 and a plurality of tubes 408 connecting the plurality of the fluid capsules 406 as shown in FIGS. 4A and 4B. Each of the fluid capsules 406 and the plurality of tubes 408 may be disposed on or close to a particular body parts (such as shoulder, elbow, wrist, chest, legs, knee, etc) as shown in FIGS. 4A and 4B. In some embodiments, each of the fluid capsules 406 and the plurality of tubes 408 may be disposed close to at least one of the plurality of second plurality of sensors 212 which may be corresponding to one body part of the rider 106.

The plurality of fluid capsules 406 may include a hardening fluid (not shown) that may be configured to flow through the plurality of tubes 408 to harden the wearable garment 112 (as shown in the fourth scenario 404 in FIG. 4B) based on the determination of the accident or the collision by the first motion information or the second motion information. Examples of the hardening fluid may include, but not limited to, a magneto-rheological fluid. The plurality of tubes 408 may be formed from a lightweight material. Examples of the lightweight material may include, but are not limited to, a flexible elastomeric tube, or a plastic tube, and the like.

In the hardening state, the control circuitry 110 may be configured to control a viscosity and/or a flow of the hardening fluid from the fluid capsules 406 through the plurality of tubes 408. The change in the viscosity of the hardening fluid may relate to increase or decrease in the rigidness of the hardening element 116 or the wearable garment 112. The flow of the hardening fluid in the plurality of tubes 408 may form fluid-cushion for the body of the rider 106 or the passenger against the impact of the accident or collision detected on the real-time basis either by the first plurality of sensors 108 disposed on the helmet 102 or the second plurality of sensors 212 disposed on the wearable garment 112. In the non-hardening state (shown in FIG. 4A), the control circuitry 110 may be configured to reset the flow of the hardening fluid from the plurality of tubes 408 back to the fluid capsule 406 to lessen the rigidness of the hardening element 116 of the wearable garment 112. Thus, based on the detection of the accident or non-accident states, the control circuitry 110 may be configured to control the rigidness of the hardening element 116 and further protect different body parts (for example i.e. chest, spin, shoulder, neck, stomach, knees, etc) of the rider 106 (or the passenger) based on the arrangement/positions of the hardening element 116 (i.e. electric fiber 402, or the combination of the fluid capsules 406 and the tubes 408) in the wearable garment 112.

In some embodiments, the control circuitry 110 may be configured to control a level of rigidness at different positions of the wearable garment 112. For example, the control circuitry 110 may control an area of the wearable garment 112 (i.e. close to certain body parts such as shoulder, elbow, spin, or knee) to become more rigid or hard as compared to other areas of the wearable garment 112 near other body parts. In some embodiments, the control circuitry 110 may be configured to determine a level of each of the second plurality of signals detected by each of the second plurality of sensors 212 disposed at the wearable garment 112. The control circuitry 110 may be further configured to control the level of rigidness of the wearable garment 112 for different body parts based on the determined level of each of the second plurality of signals. For example, in case, the determined acceleration (or G-force, or impact) detected by a first sensor (say near right elbow) of the second plurality of sensors 212 is more that the determined acceleration detected by a second sensor (say near left elbow) of the second plurality of sensors 212, then the control circuitry 110 may control the wearable garment 112 to become more rigid or harder near the first sensor than the second sensor. In some embodiments, the wearable garment 112 may include orientation sensors (not shown) to detect the orientation or direction of fall of the rider 106 or the passenger during the accident or collision, and the control circuitry 110 may control the level of rigidness of the wearable garment 112 near different body parts based on the detected orientation or direction of the fall of the rider 106 or the passenger.

In accordance with an embodiment, the helmet 102 may include the fluid capsules 406 and the plurality of tubes 408 as disposed in the wearable garment 112. The fluid capsules 406 in the helmet 102 may also include a treatment fluid (not shown) that may flow through the plurality of tubes 408 in the helmet 102. The control circuitry 110 may be configured to control the flow of the treatment fluid from the fluid capsule 406 to the plurality of tubes 408 based on a detection of temperature in the helmet 102. The control circuitry 110 may be configured to detect a sudden change in the temperature in the helmet 102 based on an electric signal received from the temperature sensor 118 located in the helmet 102. The control circuitry 110 may be configured to detect whether the sudden change in temperature in the helmet 102 is over a predefined temperature threshold, and further control cooling of the treatment fluid filled in the plurality of tubes 408 in the helmet 102 based on the detection. Thus, during the detection of the accident or collision (based on the first motion information or the second motion information) and detection of high-temperature inside the helmet 102, the disclosed system 100 or the control circuitry 110 may reduce the temperature inside the helmet 102 through cooling of the treatment fluid and may further provide real-time safety or medical assistance to the rider 106 or the passenger.

In some embodiments, the wearable garment 112 may include a plurality of temperature sensors (not shown) to detect the temperature near different body parts of the rider 106 or the passenger. The control circuitry 110 may detect the temperature near different body parts based on a plurality of electric signal received from the plurality of temperature sensors disposed in the wearable garment 112. The control circuitry 110 may further control the temperature of the treatment fluid that may flow in in at least one of the fluid capsules 406 and in at least one of the plurality of tubes 408 in the wearable garment 112 based on the temperature detected near different body parts by the plurality of temperature sensors in the wearable garment 112. In some embodiments, the control circuitry 110 may control the temperature of the treatment fluid in the wearable garment 112, based on the determined levels of the second motion information (i.e. acceleration, G-force, vibration, or impact) indicated by the second plurality of signals captured by the second plurality of sensor 212 in the wearable garment 112. Thus, the control circuitry 110 may either increase (i.e. heat) or decrease (i.e. cool) the temperature of the treatment fluid based on the detected temperature close to different body parts such that real-time medication or assistance may be provided to the body parts affected by the impact of the accident or the collision.

In another embodiment, the plurality of tubes 408 may include a dual tube structure (not shown) that may include both the hardening fluid and the treatment fluid. The control circuitry 110 may be configured to control the flow of the hardening fluid and the treatment fluid from the fluid capsule 406 to the plurality of tubes 408 based on the signal received from the first plurality of sensors 108, the second plurality of sensors 212, the temperature sensor 118 located in the helmet 102, and/or the plurality of temperature sensors located in the wearable garment 112.

In accordance with an embodiment, at least one of the first plurality of signals may be a brainwave signal captured by at least one the first plurality of sensors 108 in the helmet 102 as described, for example, in FIG. 1. The brainwave signal may indicate an emotional state of the rider 106 and/or the passenger wearing the helmet 102 during a driving state of the vehicle 104. Examples of the emotional state of the rider 106 and/or the passenger may include, but are not limited to, a stressed state, a sleep state, a nervousness state, an angry state, a sad state, or a confused state. The control circuitry 110 may be configured to capture the brainwave signal and determine the emotional state of the rider 106 or the passenger. The control circuitry 110 may be further configured to control one of the inflation element 114 or the hardening element 116 (as described in FIGS. 3A-3B and 4A-4B) disposed in the wearable garment 112 based on a determination that the emotional state may be one of the stressed state, the sleep state, the nervousness state, the angry state, the sad state, or the confused state. Thus, the disclosed system 100 or the control circuitry 110 may predict or anticipate a situation of the accident or collision that may happen based on the current emotional state of the rider 106 and may timely control the inflation element 114 or the hardening element 116 to provide safety assistance to the rider 106 before the detection or actual instance of the accident or the collision with the helmet 102 or the wearable garment 112.

In accordance with an embodiment, the helmet 102 may further include the image capturing device 120 and the location sensor 122 as described and shown, for example, in FIG. 1. The image capturing device 120 may be configured to capture the one or more images of the surroundings of the helmet 102 of the rider 106 and/or the passenger. The location sensor 122 may be configured to determine the current geo-location of the helmet 102 of the rider 106 and/or the passenger.

The control circuitry 110 in the system 100 may be configured to determine the impact of accident or collision based on the first plurality of signals or the second plurality of signals. Based on the determination of the impact of the accident, the control circuitry 110 may control the image capturing device 120 to capture the one or more images of the surroundings of the helmet 102 or the vehicle 104, and control the location sensor 122 to determine the current geo-location of the helmet 102 or the vehicle 104. The control circuitry 110 may further receive the captured one or more images information from the image capturing device 120 and the current geo-location from the location sensor 122. The control circuitry 110 may be further configured to transmit the captured one or more images of the surroundings of the helmet 102 and the determined geo-location of the helmet 102 of the rider 106 and/or the passenger to an electronic control device (ECD) of another vehicle which may located at defined distance (for example within 500 meters) from the determined geo-location of the vehicle 104. For example, in case the vehicle 104 is at a blind-spot area at the time of determination of the accident, then by the transmission of the determined current geo-location and the captured one or more images of the surrounding, the control circuitry 110 may alert the nearby vehicles to seek help and assistance. In some embodiments, the control circuitry 110 may transmit the captured images and the geo-location to nearby hospital or a police control room for assistance. The control circuitry 110 may also transmit the captured images or the geo-location to a predefined person (for example family member) to seek assistance.

In another embodiment, the control circuitry 110 may continuously control the image capturing device 120 to capture the one or more images of the surroundings and transmit the captured images to the nearby vehicles (for example another vehicle following the vehicle 104). Thus, based on the continues transmission of the captured images, the disclosed system 100 or the control circuitry 110 may alert the nearby vehicles about current situation near the vehicle 104 and may provide safety assistance to other nearby vehicles.

In accordance with an embodiment, the helmet 102 may further include the lighting element 124 as shown, for example, in FIG. 1. Based on the determination of the impact of the accident (i.e. determined based on the first plurality of signals or the second plurality of signals), the control circuitry 110 may be configured to control a first lighting pattern of the lighting element 124. The first lighting pattern may be a predefined pattern, for example, blinking at a particular frequency. In some embodiments, the control circuitry 110 may control the speaker 210 to reproduce a predefined sound pattern based on the determination of the impact of the accident. Thus, at the time of the accident, the control of the lighting element 124 and/or the speaker 210 by the disclosed system 100 may alert nearby people or vehicle to seek attention and assistance on the real-time basis.

In accordance with an embodiment, the helmet 102 may further include the media rendering device 206 as described, for example, in FIG. 1. Based on the determination of the impact of the accident or collision, the control circuitry 110 may be configured to render a predefined media content (such as pictures, video content, audio content) on the media rendering device 206. The media rendering device 206 may include the display screen 208 and the speaker 210. Thus, in case of the accident, the disclosed system 100 may render predefined media content (for example pictures of family members of the rider 106, favorite song, or movie clip of favorite celebrity) and further provide assistance to the rider 106 psychologically or control the emotional state of the rider 106 on the real-time basis.

Figure 5:
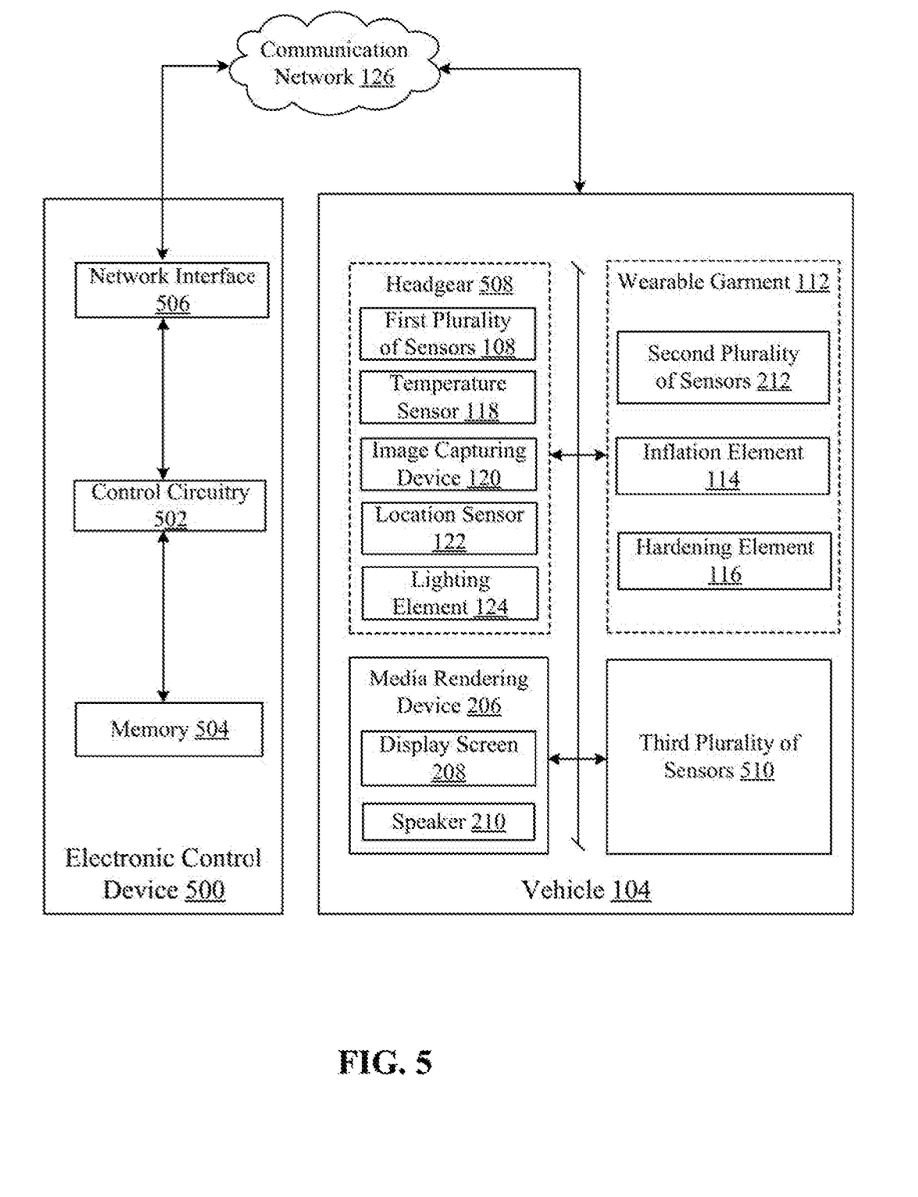
FIG. 5 illustrates a block diagram of an exemplary electronic control device of a vehicle for providing safety assistance, in accordance with an embodiment of the disclosure.

FIG. 5 illustrates a block diagram of an exemplary electronic control device of a vehicle for providing safety assistance, in accordance with an embodiment of the disclosure. FIG. 5 is explained in conjunction with elements from FIGS. 1, 2, 3A, 3B, 4A, and 4B. With reference to FIG. 5, there is shown an electronic control device 500. The electronic control device 500 may include a control circuitry 502, a memory 504, and a network interface 506. The control circuitry 502 may have a similar function of the control circuitry 110 as described, for example, in FIGS. 1 and 2. The functions of the control circuitry 502, the memory 504, and the network interface 506 may be same as the functions of the control circuitry 110, the memory 202, and the network interface 204 as described, for example, in FIGS. 2, 3A-3B, and 4A-4B. Therefore, the description of the control circuitry 502, the memory 504, and the network interface 506 is omitted from the disclosure for the sake of brevity. The control circuitry 502 may be communicably coupled with a headgear 508 and the wearable garment 112 which may be included in the vehicle 104 as shown in FIG. 5. In some embodiments, the functions of the headgear 508 may be similar to the functions of the helmet 102 as described in detail, for example, in FIGS. 1, 2, 3A-3B, and 4A-4B. Thus, the headgear 508 may include the first plurality of sensors 108, the temperature sensor 118, the image capturing device 120, the location sensor 122, the lighting element 124, and the media rendering device 206. In another embodiment, the headgear 508 may not be integrated inside the vehicle 104 and may be communicably coupled with the vehicle 104. In an embodiment, the image capturing device 120, the location sensor 122, the lighting element 124, and the media rendering device 206 may be part of the vehicle 104 and may be communicably coupled with the headgear 508. As shown in FIG. 5, the wearable garment 112 may include the second plurality of sensors 212, the inflation element 114, and the hardening element 116 as described in detail, for example, in FIGS. 1, 2, 3A-3B, and 4A-4B. In some embodiment, the wearable garment 112 may not be part of the vehicle 104, but may be communicably coupled with the vehicle 104.

The electronic control device 500 may include suitable logic, circuitry, and/or interfaces that may be configured to provide safety assistance to the rider 106. The electronic control device 500 may be a specialized electronic circuitry that may include an electronic control unit (ECU) processor to control different functions, such as, but not limited to, engine operations, communication operations, and data acquisition of the vehicle 104. The electronic control device 500 or the control circuitry 502 may be coupled with the headgear 508 and the wearable garment 112. The electronic control device 500 may be configured to capture the first plurality of signals from the first plurality of sensors 108 in the headgear 508. The first plurality of signals may indicate the first motion information corresponding to the headgear 508 as described, for example, in FIGS. 1 and 3A-3B. The electronic control device 500 may be further configured to control one of the inflation element 114 or the hardening element 116 disposed in the wearable garment 112 based on the determination that the first motion information corresponding to the headgear 508 exceeds the first predefined threshold as described in detail, for example, in FIGS. 1 and 3A-3B. In some embodiments, the electronic control device 500 may capture the second plurality of signals (which may indicate the second motion information) from the second plurality of sensors 212 in the wearable garment 112 and further control one of the inflation element 114 or the hardening element 116 as described in detail, for example, in FIGS. 4A and 4B. It may be noted that the function of the electronic control device 500 may be same as the function of the electronic control device 128 indicated in FIG. 1.

In some embodiments, the electronic control device 500 may be a microprocessor. Other examples of the electronic control device 500 may include, but are not limited to, a vehicle control system, an in-vehicle infotainment (IVI) system, an in-car entertainment (ICE) system, an automotive Head-up Display (HUD), an automotive dashboard, an embedded device, a smartphone, a human-machine interface (HMI), a computer workstation, a handheld computer, a cellular/mobile phone, a portable consumer electronic (CE) device, a server, and other computing devices. In some embodiments, the electronic control device 500 may be included or integrated in the vehicle 104.

As shown in FIG. 5, the vehicle 104 may include a third plurality of sensors 510. The functions of the third plurality of sensors 510 may be similar to the first plurality of sensors 108 and the second plurality of sensors 212. The electronic control device 500 may control the third plurality of sensors 510 to capture a third plurality of signals which may indicate third motion information with respect to the vehicle 104. The electronic control device 500 or the control circuitry 502 may be configured to detect the accident or collision based on the determination that the third motion information exceed to a third predefined threshold (similar to the first predefined threshold or the second predefined threshold). In some embodiments, values of the first predefined threshold, the second predefined threshold, and the third predefined threshold may be different because the positions of each of the first plurality of sensors 108, the second plurality of sensors 212, and the third plurality of sensors 510 are different. For example, the first plurality of sensors 108 may be disposed on the headgear 508, the second plurality of sensors 212 may be disposed on the wearable garment 112, and the third plurality of sensors 510 may be disposed on the vehicle 104. Thus, the predefined thresholds of each sensor to detect the impact or shock of accident may be different.

The disclosed system 100 or the electronic control device 500 may have the capability to detect the accident or collision based on the signals provided by either of the first plurality of sensors 108, the second plurality of sensors 212, and the third plurality of sensors 510, and further control one of the inflation element 114 or the hardening element 116 based on the determination if either of the first motion information exceeds the first predefined threshold, the second motion information exceeds the second predefined threshold, or the third motion information exceeds the third predefined threshold.

Figure 6:
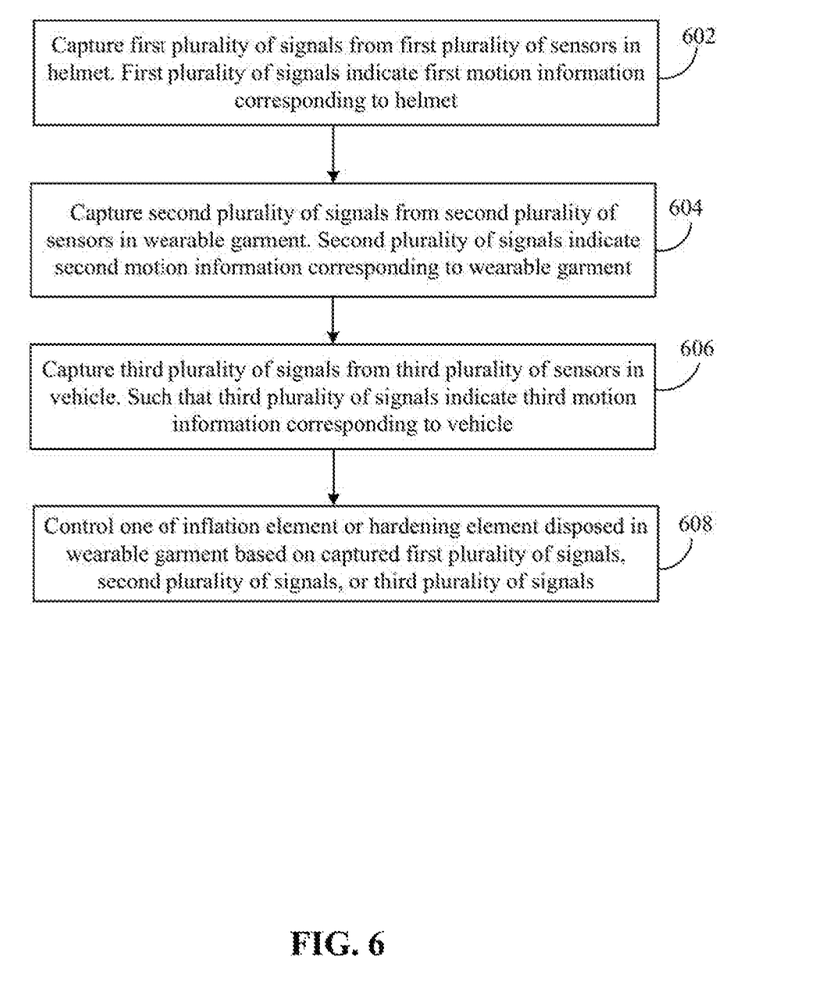
FIG. 6 illustrates a flowchart of an exemplary method for providing safety assistance in a vehicle, in accordance with an embodiment of the disclosure.

FIG. 6 illustrates a flowchart of an exemplary method for providing safety assistance in a vehicle, in accordance with an embodiment of the disclosure. FIG. 6 is explained in conjunction with elements from FIGS. 1, 2, 3A, 3B, 4A, 4B, and 5. With reference to FIG. 6, there is shown a flowchart 600 that depicts a method for providing safety assistance in the vehicle 104. Any computing device, for example, control circuitry 110 or the control circuitry 502, may execute operations specified in the method. The method illustrated in the flowchart 600 may start from 602.

At 602, the first plurality of signals may be captured from the first plurality of sensors 108 in the helmet 102. The first plurality of signals may indicate the first motion information corresponding to the helmet 102. In accordance with an embodiment, the control circuitry 110 or the control circuitry 502 may be configured to capture the first plurality of signals from the first plurality of sensors 108 in the helmet 102, such that first plurality of signals may indicate first motion information corresponding to the helmet 102. The capture of the first plurality of signals and the first motion information is described, in detail, for example, in FIGS. 1, 3A, and 3B.

At 604, the second plurality of signals may be captured from the second plurality of sensors 212 in the wearable garment 112. The second plurality of signals may indicate the second motion information corresponding to the wearable garment 112. In an embodiment, the control circuitry 110 or the control circuitry 502 may be configured to capture the second plurality of signals from the second plurality of sensors 212 in wearable garment 112, such that second plurality of signals may indicate the second motion information corresponding to wearable garment 112 as described, for example, in FIGS. 4A, 4B, and 5.

At 606, the third plurality of signals may be captured from the third plurality of sensors 510 in the vehicle 104. The third plurality of signals may indicate the third motion information corresponding to the vehicle 104. In an embodiment, the control circuitry 110 or the control circuitry 502 may be configured to capture the third plurality of signals from the third plurality of sensors 510 in the vehicle 104 (or disposed on the vehicle 104).

At 608, one of the inflation element 114 or the hardening element 116 disposed in the wearable garment 112 may be controlled based on the captured first plurality of signals, the second plurality of signals, or the third plurality of signals. In an embodiment, the control circuitry 110 or the control circuitry 502 may be configured to control one of the inflation element 114 or the hardening element 116 disposed in the wearable garment 112 based on the determination that the first motion information corresponding to the helmet 102 exceeds the first predefined threshold, or the second motion information corresponding to the wearable garment 112 exceeds the second predefined threshold, or the third motion information corresponding to the vehicle 104 exceeds the third predefined threshold.

The flowchart 600 is illustrated as discrete operations, such as 602, 604, 606 and 608. However, in certain embodiments, such discrete operations may be further divided into additional operations, combined into fewer operations, or eliminated, depending on the particular implementation without detracting from the essence of the disclosed embodiments.

For the purposes of the present disclosure, expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural. Further, all joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent devices by those of ordinary skill in the art. Rather it is hereby intended the scope be defined by the claims appended hereto. Additionally, the features of various implementing embodiments may be combined to form further embodiments.

The invention claimed is:

1. A system, comprising:
   a helmet;
   a first plurality of sensors in the helmet; and
   control circuitry configured to:
      capture a first plurality of signals from the first plurality of sensors in the helmet, wherein the first plurality of signals indicate first motion information corresponding to the helmet; and
      control a hardening element disposed in a wearable garment based on a determination that the first motion information corresponding to the helmet exceeds a first predefined threshold, wherein the hardening element comprises an electric fiber woven on the wearable garment, and wherein the control circuitry is further configured to control rigidity of the hardening element based on the determination.

2. The system according to claim 1, wherein the hardening element include a hardening fluid and wherein the control circuitry is further configured to change viscosity of the hardening fluid to increase or decrease rigidity of the hardening element based on the determination.

3. The system according to claim 1, wherein the first plurality of sensors comprises one of an acceleration sensor, a speed sensor, a G-force sensor, a vibration sensor, an impact sensor, a shock sensor, or an elevation sensor.

4. The system according to claim 1, wherein the first motion information indicates a sudden change in acceleration, in one of a X-direction, a Y-direction, or a Z-direction, used to detect an accident or a collision with the helmet or with a vehicle.

5. The system according to claim 1, further comprising a temperature sensor in the helmet, wherein the control circuitry is further configured to:
   detect a change in temperature in the helmet through the temperature sensor, and
   control cooling of a treatment fluid filled in a tube inside the helmet based on the detected change in the temperature in the helmet over a predefined temperature threshold.

6. The system according to claim 1,
   wherein at least one of the first plurality of signals is a brainwave signal to indicate an emotional state of a wearer of the helmet during a driving state of a vehicle, and
   wherein the control circuitry is further configured to control one of the inflation element or the hardening element disposed in the wearable garment based on a determination that the emotional state is one of a stressed state, a sleep state, a nervousness state, an angry state, a sad state, or a confused state.

7. The system according to claim 1, further comprising a media rendering device, wherein the control circuitry is further configured to render a predefined media content on the media rendering device based on the determination.

8. The system according to claim 7, wherein the media rendering device comprises one of a display screen or a speaker.

9. The system according to claim 1, further comprising:
   an image capturing device disposed on the helmet; and
   a location sensor in the helmet,
      wherein, based on the determination, the control circuitry is further configured to:
         control the image capturing device to capture one or more images of surroundings of the helmet,
         control the location sensor to determine a geo-location of the helmet, and transmit the captured one or more images and the determined geo-location to an electronic control device of a vehicle located at defined distance from the determined geo-location.

10. The system according to claim 1, further comprising a lighting element disposed on the helmet, wherein the control circuitry is further configured to control a first lighting pattern of the lighting element based on the determination.

11. The system according to claim 1, wherein the control circuitry is further configured to control the hardening element disposed in the wearable garment via one of a wired connection or a wireless connection.

12. An electronic control device, comprising:
   control circuitry communicably coupled with a headgear and a wearable garment, wherein the control circuitry is configured to:
      capture a first plurality of signals from a first plurality of sensors in the headgear, wherein the first plurality of signals indicate first motion information corresponding to the headgear;
      control an inflation element disposed in the wearable garment based on a determination that the first motion information corresponding to the headgear exceeds a first predefined threshold;
      capture a second plurality of signals from a second plurality of sensors disposed on the wearable garment;
      wherein each of second plurality of signals indicates second motion information corresponding to each of the second plurality of sensors associated with a body part of a wearer of the wearable garment;
      wherein the wearable garment includes a plurality of tubes filled with a treatment fluid, wherein each of the plurality of tubes is disposed on the corresponding body part with which the corresponding second plurality of sensors are associated, and
      wherein the circuitry is further configured to control temperature of the treatment fluid filled in at least one tube of the plurality of tubes based on the captured second plurality of signals.

13. The electronic control device according to claim 12, wherein the inflation element comprises an inflation chamber which inflates based on a signal received from the control circuitry in the helmet.

14. The electronic control device according to claim 12, wherein the control circuitry is further configured to receive a third plurality of signals from a third plurality of sensors disposed in a vehicle which includes the headgear and the wearable garment.

15. A method, comprising:
   in control circuitry:
      capturing a first plurality of signals from a first plurality of sensors in a helmet, wherein the first plurality of signals indicate first motion information corresponding to the helmet; and
      controlling a hardening element disposed in a wearable garment based on a determination that the first motion information corresponding to the helmet exceeds a first predefined threshold, wherein the hardening element comprises an electric fiber woven on the wearable garment, and wherein the control circuitry is further configured to control rigidness of the hardening element based on the determination.

* * * * *